United States Patent
Schneider et al.

(10) Patent No.: US 7,028,690 B2
(45) Date of Patent: Apr. 18, 2006

(54) COMPRESSION SUPPORT STOCKING WITH A COMPRESSION SUPPORT BODY

(76) Inventors: Thomas Schneider, Erich-Honsteinstrasse 38, Eisenach (DE) 99817; Ulrich Schindewolf, Erich-Honsteinstrasse 38, Eisenach (DE) 99817; Thomas Haerer, Spessartstrasse 3, Bad Hersfeld (DE) 36251

( * ) Notice: Subject to any disclaimer, the term of this patent is extended or adjusted under 35 U.S.C. 154(b) by 295 days.

(21) Appl. No.: 10/638,558

(22) Filed: Aug. 12, 2003

(65) Prior Publication Data

US 2004/0106887 A1    Jun. 3, 2004

(30) Foreign Application Priority Data

Aug. 12, 2002 (DE) ............................... 102 37 374

(51) Int. Cl.
*A61F 5/37* (2006.01)

(52) U.S. Cl. ...................................... 128/882

(58) Field of Classification Search ................. 602/60, 602/61, 62, 42, 75; 2/239, 240, 241, 242
See application file for complete search history.

(56) References Cited

U.S. PATENT DOCUMENTS

| 4,700,698 | A | | 10/1987 | Kleylein |
| 5,711,029 | A | * | 1/1998 | Visco et al. ...................... 2/24 |
| 6,129,694 | A | | 10/2000 | Bodenschatz |
| 6,279,160 | B1 | * | 8/2001 | Chen ................................ 2/24 |

FOREIGN PATENT DOCUMENTS

| DE | 1 929 624 U | 12/1965 |
| DE | 3412772 | 10/1985 |
| DE | 3637879 | 5/1988 |
| DE | 38 38 576 A1 | 5/1991 |
| DE | 9317021 | 3/1994 |
| DE | 628297 B1 | 5/1994 |
| DE | 4341722 | 6/1994 |
| DE | 598291 A1 | 12/1994 |
| DE | 19506128 | 10/2000 |
| EP | 0027172 | 4/1981 |
| EP | 0262638 | 4/1988 |
| EP | 0 598 291 A1 | 5/1994 |
| EP | 0 628 297 B1 | 12/1994 |

* cited by examiner

*Primary Examiner*—Henry Bennett
*Assistant Examiner*—Camtu Nguyen
(74) *Attorney, Agent, or Firm*—Crowell & Moring LLP

(57) ABSTRACT

A compression stocking (1) made of a knit or woven elastic fabric provided with a compression body (6) which can be attached to the compression stocking (1) such that the compression body is positioned at a knee joint (5). The compression stocking (1) of the invention can be used, for example, after surgery in the area of the knee joint (5). To get rid of the wound secretion, blood and tissue fluid that occurs during surgery from the soft tissue surrounding the joint, a defined pressure is applied by the compression stocking (1) and the compression body (6) to the soft tissue of the knee joint (5). To this end, the compression body (6) has a recess (7) to accommodate the patella of the knee joint (5). The recess (7) and the compression body (6) each have an elliptical shape, which is approximately adapted to the shape of the patella, i.e., the joint soft tissue. To accommodate the wound suture and associated wound clamps, the compression body (6) has a groove-shaped recess (11) on the surface facing the soft tissue of the knee joint (5).

10 Claims, 1 Drawing Sheet

COMPRESSION SUPPORT STOCKING WITH A COMPRESSION SUPPORT BODY

BACKGROUND OF THE INVENTION

The present invention relates to compression support stocking made of a woven or knit elastic fabric having a compression support body made of a resilient material that can be attached to the compression support stocking.

Compression support stockings are well known in practice, comprised essentially of a knit or woven elastic fabric running the entire length of the leg. Compression stockings and hose are used for various venous diseases, e.g., varicose veins. Compression stockings produce a consistent acceleration of venous blood flow to the heart and eliminate venous congestion. Pathological malfunctioning of venous valves is corrected from the outside through the compression effect, because the pumping action of the calf muscle pump is restored. In addition, this prevents spent blood and tissue fluid from collecting in the tissue and forming congestion, so the tissue is protected from the damage of progressive edema. Compression stockings thus may also be used in the prevention of thrombosis, e.g., after a surgical procedure.

A compression stocking of the aforementioned type is known from German Patent Application No. DE 195 06 128 A1. This published patent application discloses a method of attaching compression bodies to compression stockings. The compression bodies are designed as resilient pressure pads or protective and supporting pads. However, the published patent application does not go into detail about the precise design, the site of attachment or the mechanism of action of the pads or support pads or the range of possible uses of the compression stocking.

In addition, German Patent Application No. DE 43 41 722 A1 describes a compression stocking having an integrated compression body designed as an insert pad for treating lymphostatic fibroses. The pad is formed by a flat resilient foam body having a plurality of elevations and indentations. As the corresponding body part moves, these elevations and indentations produce a mechanical stimulus effect on the pathological tissue, thus permitting or improving the return flow of congested tissue fluid even under pathological conditions.

It has proven to be a disadvantage that the foam material always attempts to return to its original shape due to its very high density and the thickness of material required. Thus, when the foam material is pressed by the surrounding compression stocking against the structure that is to be compressed, a restoring force is created by the foam material, opposing the movement of the respective body part. This greatly restricts the patient's freedom of movement.

European Patent No. EP 27,172 A1 and European Patent No. EP 262,638 A2 both describe a tubular bandage for supporting, i.e., compressing joints. This tubular bandage is pulled over the respective joint in the event of a joint injury. It has a ring-shaped compression insert surrounding the bony projections of the joint. This compression insert exerts pressure on the soft tissue of the joint, thereby producing a mechanical stimulus, which helps to reduce swelling of the injured joint and/or joint soft tissue. These bandages are used after injuries or in degenerative diseases, e.g., when there is damage to the meniscus, in arthrosis and effusion and ligament injuries of the knee joint. The pressure exerted by the bandage is applied exclusively to the compression insert and thus exclusively to the soft tissue of the joint.

SUMMARY OF THE INVENTION

The object of this invention is to provide a compression support stocking with an improved effect.

Another object of the invention it to provide a compression support stocking with a wider range of applications.

These and other objects are achieved in accordance with the present invention by providing a compression support stocking made of a knit or woven elastic fabric and having a compression body made of a resilient material attachable thereto, wherein the compression body is provided with a central recess for accommodating the patella of a knee joint; said compression body exerting a pressure on soft tissue adjacent the knee joint, and wherein a surface of the compression body facing the knee joint is provided with at least one groove-shaped recess.

Further aspects and preferred embodiments of the invention are described hereinafter.

This invention thus relates to a compression stocking in which the compression body has a recess to accommodate the patella of a knee joint. A pressure can be exerted on the adjacent soft tissue of the joint by means of the compression body surrounding the recess, and a surface of the compression body facing the joint soft tissue has at least one groove-shaped recess. This makes it possible to also use the inventive compression stocking immediately following a surgical procedure in the area of the knee joint. The complex and tedious wrapping of the knee joint with elastic bandages, which was considered necessary in the prior art to apply pressure to the knee joint and the leg, is thus no longer necessary.

With the inventive compression stocking, a defined pressure is exerted simultaneously on both the enclosed leg and the compression body. The patella of the knee joint is not subjected to a compressive force due to the recess in the compression body. Instead, the pressure is introduced entirely into the soft tissue of the joint surrounding the patella. This forces the wound secretion, blood and tissue fluid that occurs after surgery back out of the soft tissue of the joint, i.e., the vascular capsule of the knee joint through the venous return flow. This prevents swelling of the knee joint and suppuration of the wound suture. The pressure exerted by the compression stocking on the adjacent areas of the leg prevents these fluids from collecting and prevents fluid congestion in the adjacent area of the leg, thereby supporting the venous return flow and preventing an imminent thrombosis.

The wound suture produced in surgery is accommodated in the recess in the compression body together with the respective wound clamps. Thus the pressure of the compression body does not act upon the wound suture, which is extremely sensitive to pain. This promotes wound healing, prevents suppuration and at the same time relieves the pain experienced by the patient. In addition, accommodating the wound suture and/or wound clamps in the compression body and arranging the patella in the recess of the compression body achieves the result that the compression body rests in surface contact with the areas of the joint where the joint soft tissue is located. Thus the entire pressure exerted by the compression stocking can be transferred via the compression body to the soft tissue of the joint.

In one especially advantageous embodiment of the invention, the compression body is designed to have an elliptical shape with a main axis and a secondary axis. Consequently, the compression body is adapted to the shape of the joint soft tissue of the knee, i.e., the vascular capsule, which has an approximately elliptical shape. The compression body is aligned so that the main axis of the compression body is approximately parallel with a longitudinal axis of the body. Adapting the compression body to the joint soft tissue in this manner ensures that the pressure applied by the compression stocking will be transferred completely to the joint soft tissue with negligible losses.

It has proven to be especially effective for the groove-shaped recess to be situated along the main axis of the compression body. In this way, the groove-shaped recess in the compression body is adapted to the typical line of sutures in knee surgery.

In practice, it has proven particularly suitable for the groove-shaped recess to be approximately 12 to 20 mm wide and approximately 4 to 10 mm deep. These dimensions of the recess are generally adequate to accommodate the wound suture in practice and also for accommodating the conventional sizes of wound clamps.

In accordance with a particularly advantageous embodiment of the invention, the recess in the compression body is designed to be elliptical. The shape of the recess in the compression body thus is adapted approximately to the shape of the patella. This improves the transfer of the force exerted by the compression body onto the adjacent joint soft tissue, and the patella is supported and guided.

In actual practice, it has proven suitable for the recess to be approximately 70 to 85 mm long, based on a main axis, and approximately 50 to 60 mm wide, relative to a secondary axis. This size range corresponds approximately to the size of the patella of a knee joint. It would be advantageous to measure the patient's patella before surgery to be able to accurately adapt or fit the recess in the compression body to the particular patella. This further improves the introduction of pressure into adjacent joint soft tissue and also further improves the supportive effect for the patella.

In accordance with another particularly advantageous refinement of this invention, the compression body is detachably attached to the compression stocking by an adhesion connection. The adhesive connection ensures a secure connection between the compression body and the compression stocking with minimal wrinkling. This results in a smooth surface in the area of contact with the knee joint, which in turn makes it possible to avoid pressure spots. The flexibility of the compression stocking is additionally increased due to the detachable attachment of the compression body, because the compression stocking can be used either with the compression body attached in postoperative use or without the compression body, e.g., exclusively for prevention of thrombosis. In addition, this permits the use of different compression bodies, e.g., for other applications, in or with one and the same compression stocking.

It has proven particularly advantageous for the compression body to be made of silicone in at least some sections. Silicone has a good compressive strength and is therefore a particularly suitable material for use as the compression body. In addition, it is very easy to disinfect silicone, which is in turn particularly advantageous when used in direct contact with a wound suture, e.g., to prevent suppuration and inflammation of the wound suture. Furthermore, silicone has been found in practice to be tolerated particularly well by skin.

In another advantageous refinement of the invention, a protective layer is arranged between the compression body and the joint soft tissue. This protective layer prevents direct contact between the compression body and the joint soft tissue and is particularly advantageous, especially for patients allergic to silicone. In addition, the protective layer also absorbs secretions coming from the wound suture and thereby improves wound healing.

BRIEF DESCRIPTION OF THE DRAWINGS

The invention will be described in further detail hereinafter with reference to illustrative preferred embodiments shown in the accompanying drawing figures in which.

DETAILED DESCRIPTION OF PREFERRED EMBODIMENTS

Figure 1:
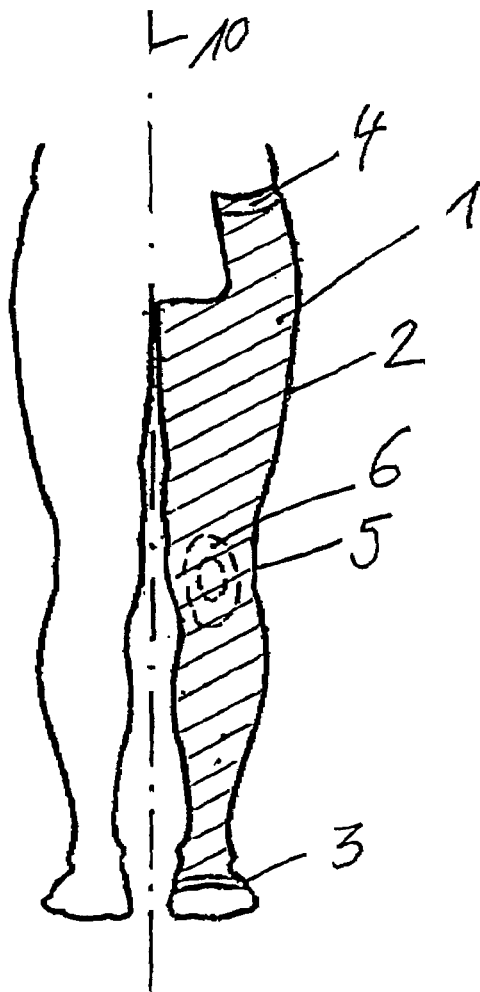
FIG. 1 is a schematic front view of a person, shown from the hips down, wearing a compression stocking according to the invention.

FIG. 1 shows a schematic front view of a person, shown from the hips down, wearing a compression stocking 1 according to the invention. The compression stocking 1 covers the entire leg 2 from the foot area 3 up to the area of the groin 4. The compression stocking is made of a woven or knit elastic fabric and is composed of different component materials, depending on the desired compression pressure. For example, the compression stocking 1 may be a compression class II compression stocking made of 65% polyamide (nylon) and 35% elasthane. However, other material compositions and compression classes of the compression stocking 1 are also conceivable.

In the area of a knee joint 5, a compression body 6 designed as a truss or support pad is disposed between the compression stocking 1 and the knee joint 5 and is attached to the inside of the compression stocking 1. The compression body 6 is shown in broken lines in FIG. 1 because it is arranged beneath the compression stocking 1. The compression stocking 1 according to this invention may be used in the postoperative field in particular, e.g., after surgery on the knee joint 5.

Figure 2:
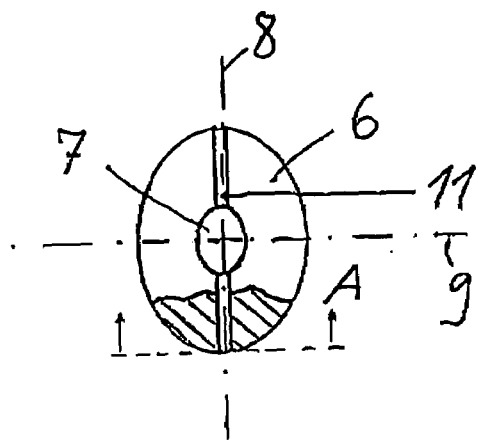
FIG. 2 is a rear view of a compression body according to FIG. 1 in an enlarged and partially cut-away diagrammatic view.

A defined pressure is exerted on the leg 2 and on the compression body 6 by the compression stocking 1. FIG. 2 shows a rear view of the compression body 6 according to FIG. 1 in an enlarged and partially sectional view. The compression body 6 has a recess 7 to accommodate the patella of the knee joint 5. This provides support and guidance for the patella and prevents it from being subjected to the pressure applied by the compression body 6.

The compression body 6 and also the recess 7 have an approximately elliptical shape with a main axis 8 and a secondary axis 9. Therefore, the shape of the compression body 6 is adapted approximately to the shape of the joint soft tissue, and the recess 7 is adapted approximately to the shape of the patella. The pressure applied by the compression stocking 1 is thus transferred via the compression body 6 completely and almost without any loss into the joint soft tissue of the knee joint 5. Consequently, wound secretions, blood and tissue fluid produced after surgery are forced out of the joint soft tissue, i.e., the vascular envelope of the knee joint 5, through the venous return flow, thereby preventing swelling of the knee joint 5. The compression stocking 1 supports this venous return flow of fluids throughout the entire area of the leg and thus prevents a thrombosis.

When the compression stocking 1 is worn as indicated in FIG. 1, the compression body 6 is arranged relative to the knee joint 5, i.e., the patella, so that the main axis 8 of the compression body 6 extends approximately parallel to a longitudinal axis 10 of the body.

Figure 3:
FIG. 3 is a view of the compression body in the viewing direction A—A shown in Figure FIG. 2.

To accommodate a wound suture and wound clamps, a groove-shaped recess 11 is provided in the compression body 6. This recess 11 is arranged along the main axis 8 of the compression body 6 along the entire length of the compression body 6 and is interrupted only by the recess 7. As can be seen, in particular, from FIG. 3, the depth of the groove or recess 11 is less than the thickness of the compression body 6.

The compression body 6 may be made of silicone or any other suitable material having similar properties.

Through the inventive compression stocking 1 provided with the compression body 5 in accordance with the invention, wound healing is improved in postoperative use, swelling of the knee is reduced or prevented and suppuration is prevented. In addition, the compression stocking also helps to prevent a thrombosis.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compression support stocking made of a knit or woven elastic fabric and having a compression body made of a resilient material attachable thereto, wherein the compression body is provided with a central recess for accommodating the patella of a knee joint; said compression body exerting a pressure on soft tissue adjacent the knee joint, and wherein a surface of the compression body facing the knee joint is provided with at least one groove-shaped recess extending alone the entire length of the compression body, said groove-shaped recess being interrupted only by said central recess.

2. A compression support stocking according to claim 1, wherein the groove-shaped recess faces the soft tissue surrounding the patella.

3. A compression support stocking according to claim 1, wherein the compression body has an elliptical shape with a longer main axis and a shorter secondary axis.

4. A compression support stocking according to claim 3, wherein the groove-shaped recess is arranged along the main axis of the compression body.

5. A compression support stocking according to claim 1, wherein the groove-shaped recess is about 12 to 20 mm wide and about 4 to 10 mm deep.

6. A compression support stocking according to claim 3, wherein the central recess in the compression body has an elliptical configuration.

7. A compression support stocking according to claim 6, wherein the central recess is about 70 to 85 mm long and about 50 to 60 mm wide.

8. A compression support stocking according to claim 1, wherein the compression body is detachably attached to the compression stocking by an adhesive connection.

9. A compression support stocking according to claim 1, wherein at least part of the compression body is made of silicone.

10. A compression support stocking according to claim 1, wherein a protective layer is arranged between the compression body and the soft tissue of the joint.

* * * * *